United States Patent

Sutton et al.

[11] Patent Number: 5,888,723
[45] Date of Patent: Mar. 30, 1999

[54] METHOD FOR NUCLEIC ACID AMPLIFICATION AND DETECTION USING ADHERED PROBES

[75] Inventors: Richard Calvin Sutton, Rochester; Ignazio Salvatore Ponticello, Pittsford; Thomas Joseph Cummins, Rochester; Dennis Roland Zander, Penfield; William Harold Donish, Rochester, all of N.Y.; Paul Hong-Dze Chen, Oak Brook, Ill.; John Bruce Findlay, Rochester, N.Y.

[73] Assignee: Johnson & Johnson Clinical Diagnostics, Inc., Rochester, N.Y.

[21] Appl. No.: 980,512

[22] Filed: Nov. 20, 1992

Related U.S. Application Data

[63] Continuation-in-part of Ser. No. 837,772, Feb. 18, 1992, Pat. No. 5,380,489.

[51] Int. Cl.[6] ............................. C12Q 1/68; C12P 19/34
[52] U.S. Cl. .................... 435/5; 435/6; 435/91.2; 435/968; 536/24.3; 436/501; 436/533; 935/78
[58] Field of Search ................ 435/6, 91, 172.3, 435/968, 5, 91.2; 436/501, 533, 807, 810; 935/78; 536/24.3

[56] References Cited

U.S. PATENT DOCUMENTS

| | | | |
|---|---|---|---|
| 4,072,769 | 2/1978 | Libel | 427/38 |
| 4,144,306 | 3/1979 | Figueras | 422/56 |
| 4,258,001 | 3/1981 | Pierce et al. | 422/56 |
| 4,357,363 | 11/1982 | Pierce et al. | 427/2 |
| 4,381,921 | 5/1983 | Pierce et al. | 436/535 |
| 4,617,468 | 10/1986 | Shiraishi et al. | 250/484.1 |
| 4,797,355 | 1/1989 | Stabinsky | 435/6 |
| 4,925,785 | 5/1990 | Wang et al. | 435/6 |
| 4,994,373 | 2/1991 | Stavrianopoulos et al. | 435/6 |
| 5,024,933 | 6/1991 | Yang et al. | 435/6 |
| 5,154,888 | 10/1992 | Zander et al. | 422/58 |

FOREIGN PATENT DOCUMENTS

| | | |
|---|---|---|
| 212670 | 3/1987 | European Pat. Off. . |
| 342586 | 11/1989 | European Pat. Off. . |
| 381501 | 8/1990 | European Pat. Off. . |
| 3717209 | 5/1987 | Germany . |

*Primary Examiner*—Carla J. Myers

[57] ABSTRACT

Nucleic acids can be amplified and detected using an element which has a sealable support on which is disposed a nucleic acid reagent composition. The composition is a mixture of a nucleic acid reagent composed of polymeric particles to which an oligonucleotide is covalently attached. The particles are prepared from a first polymer having a glass transition temperature of at least about 70° C. and have an average diameter of from about 0.1 to about 3 micrometers. The reagent is adhered to the support using a water insoluble adhesive comprising a second polymer which has a glass transition temperature which is at least about 30° C. less than the glass transition temperature of the first polymer. The adhesive is present in the composition at from about 1 to about 20 dry weight percent. The method provides high sensitivity and low background in the assay of nucleic acids, preferably using polymerase chain reaction.

24 Claims, 1 Drawing Sheet

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Probe oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:1:

GAGACCATCA ATGACGAAGC TGCAGAAT      2 8

( 2 ) INFORMATION FOR SEQ ID NO:2:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: DNA Primer ( i i i ) HYPOTHETICAL: No ( i v ) ANTI-SENSE: No ( v i ) ORIGINAL SOURCE: Synthetically prepared ( v i i ) IMMEDIATE SOURCE: Same prepared ( x ) PUBLICATION INFORMATION: None ( x i ) SEQUENCE DESCRIPTION: SEQ ID NO:2:

AGTGGGGGGA CATCAAGCAG CCATGCAA 28

( 2 ) INFORMATION FOR SEQ ID NO:3:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: DNA Primer ( i i i ) HYPOTHETICAL: No ( i v ) ANTI-SENSE: No ( v i ) ORIGINAL SOURCE: Synthetically prepared ( v i i ) IMMEDIATE SOURCE: Same prepared ( x ) PUBLICATION INFORMATION: None ( x i ) SEQUENCE DESCRIPTION: SEQ ID NO:3:

TTCCTGCTAT GTCACTTCCC CTTGGTTC 28

( 2 ) INFORMATION FOR SEQ ID NO:4:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Probe oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Same prepared ( x ) PUBLICATION INFORMATION: None ( x i ) SEQUENCE DESCRIPTION: SEQ ID NO:4:

ATTATCTTTT ATATTCTAAC CAGGATT 27

( 2 ) INFORMATION FOR SEQ ID NO:5:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Same prepared (x) PUBLICATION INFORMATION: None (xi) SEQUENCE DESCRIPTION: SEQ ID NO:5:

AATCCTGGTT AGAATATAAA AGATAAT                                27

(2) INFORMATION FOR SEQ ID NO:6:

(i) SEQUENCE CHARACTERISTICS:
      (A) LENGTH: 41 nucleotides
      (B) TYPE: Nucleic acid
      (C) STRANDEDNESS: Single
      (D) TOPOLOGY: Linear (ii) MOLECULE TYPE: Probe oligonucleotide (iii) HYPOTHETICAL: No (iv) ANTI-SENSE: No (vi) ORIGINAL SOURCE: Synthetically prepared (vii) IMMEDIATE SOURCE: Same prepared (x) PUBLICATION INFORMATION: None (xi) SEQUENCE DESCRIPTION: SEQ ID NO:6:

ATCCTGGGAT TAAATAAAAT AGTAAGAATG TATAGCCCTA C              41

(2) INFORMATION FOR SEQ ID NO:7:

(i) SEQUENCE CHARACTERISTICS:
      (A) LENGTH: 31 nucleotides
      (B) TYPE: Nucleic acid
      (C) STRANDEDNESS: Single
      (D) TOPOLOGY: Linear (ii) MOLECULE TYPE: Probe oligonucleotide (iii) HYPOTHETICAL: No (iv) ANTI-SENSE: No (vi) ORIGINAL SOURCE: Synthetically prepared (vii) IMMEDIATE SOURCE: Same prepared (x) PUBLICATION INFORMATION: None (xi) SEQUENCE DESCRIPTION: SEQ ID NO:7:

CCTCAAACAG ACACCATGGT GCACCTGACT C                         31

(2) INFORMATION FOR SEQ ID NO:8:

(i) SEQUENCE CHARACTERISTICS:
      (A) LENGTH: 28 nucleotides
      (B) TYPE: Nucleic acid
      (C) STRANDEDNESS: Single
      (D) TOPOLOGY: Linear (ii) MOLECULE TYPE: HIV-I DNA primer (iii) HYPOTHETICAL: No (iv) ANTI-SENSE: No (vi) ORIGINAL SOURCE: Synthetically prepared (vii) IMMEDIATE SOURCE: Same prepared (x) PUBLICATION INFORMATION: None (xi) SEQUENCE DESCRIPTION: SEQ ID NO:8:

```
TTTGGTCCTT   GTCTTATGTC   CAGAATGC                                                                        2 8
```

( 2 ) INFORMATION FOR SEQ ID NO:9:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: HIV-I DNA primer ( i i i ) HYPOTHETICAL: No ( i v ) ANTI-SENSE: No ( v i ) ORIGINAL SOURCE: Synthetically prepared ( v i i ) IMMEDIATE SOURCE: Same prepared ( x ) PUBLICATION INFORMATION: None ( x i ) SEQUENCE DESCRIPTION: SEQ ID NO:9:

```
ATAATCCACC   TATCCCAGTA   GGAGAAAT                                                                        2 8
```

METHOD FOR NUCLEIC ACID AMPLIFICATION AND DETECTION USING ADHERED PROBES

This application is a continuation-in-part of U.S. Ser. No. 07/837,772, filed on Feb. 18, 1992, now U.S. Pat. No. 5,380,489.

FIELD OF THE INVENTION

This invention relates to a method for the amplification and detection of nucleic acids using an element having an oligonucleotide attached thereto. This invention is particularly directed to the field of nucleic acid diagnostics.

BACKGROUND OF THE INVENTION

Nucleic acid probe technology has developed rapidly in recent years as researchers have discovered its value for detection of various diseases, organisms or genetic features which are present in small quantities in a human or animal test sample. The use of probes is based upon the concept of complementarity. DNA has two strands bound together by hydrogen bonds between complementary nucleotides (which are also known as nucleotide pairs). The DNA complex is normally stable, but the strands can be separated (or denatured) by conditions which disrupt the hydrogen bonding. The released single strands will reassociate only with another strand having a complementary sequence of nucleotides. This hybridization process can occur with both strands being in solution or with one of the strands being attached to a solid substrate.

A target nucleic acid sequence in an organism or cell may be only a very small portion of the entire DNA molecule so that it is very difficult to detect its presence using most labeled DNA probes. Much research has been carried out to find ways to detect only a few molecules of a target nucleic acid.

A significant advance in the art is described in U.S. Pat. No. 4,683,195 (Mullis et al), U.S. Pat. No. 4,683,202 (Mullis) and U.S. Pat. No. 4,965,188 (Mullis et al). These patents describe amplification and detection methods wherein primers are hybridized to the strands of a target nucleic acid (considered the templates) in the presence of a nucleotide polymerization agent (such as a DNA polymerase) and deoxyribonucleoside triphosphates. Under specified conditions, the result is the formation of primer extension products as nucleotides are added along the templates from the 3'-end of the primers. These products are then denatured and used as templates for more of the same primers in another extension reaction. When this cycle of denaturation, hybridization and primer extension is carried out a number of times (for example 25 to 30 cycles), the process which is known as "polymerase chain reaction" (or PCR) exponentially increases the original amount of target nucleic acid so that it is readily detected.

Once the target nucleic acid has been sufficiently amplified, various detection procedures can be used to detect it, as noted in the cited patents.

Various devices have been designed for hybridization assays whereby a target nucleic acid is insolubilized prior to detection using appropriate detection probes. For example, nitrocellulose filters and other planar, solid supports have been used for this purpose as described for example, in U.S. Pat. No. 4,925,785 (Wang et al).

One technique used to attach probes or other reagents is merely to dry them down onto the solid support, as described for example in EP-A-0 381 501 (published Aug. 8, 1990). More recently, probes attached to polymeric particles are fused into a solid support formed of another polymer which can be softened by heat (see U.S. Ser. No. 639,454, filed Jan. 10, 1991 by Zander et al).

While providing improvement over prior techniques, immobilization of capture reagents (such as capture probes) by drying or fusing has limitations. Adhesion of the reagents is poor. Particularly in assays whereby reagents in solution are washed over the immobilized capture probes, some of the probes are dislodged and potential signal is lost when the probes are washed away. Moreover, fusion of capture probes to a solid support requires high temperatures and dangerous equipment which tend to reduce the ability of the probes to capture a target nucleic acid.

It would be desirable to avoid the problems associated with known means for immobilizing capture probes while providing highly sensitive assays with minimal loss in signal associated with loss of capture probe.

SUMMARY OF THE INVENTION

The problems noted above have been solved with a method for the detection of a target nucleic acid comprising:

A. contacting a specimen suspected of containing a target nucleic acid with a nucleic acid test element comprising a sealable support having disposed thereon a nucleic acid reagent composition comprising a mixture of:
   a. a nucleic acid reagent comprising:
      particles composed of a first polymer having a glass transition temperature of at least about 70° C., the particles having an average diameter of from about 0.1 to about 3 micrometers, and
      an oligonucleotide covalently attached to the particles which is complementary to the target nucleic acid, and
   b. a water insoluble adhesive comprising a second polymer which has a glass transition temperature which is at least about 30° C. less than the glass transition temperature of the first polymer,
   the polymeric adhesive being present in the composition at from about 1 to about 20 dry weight percent,
   so as to form a water insoluble hybridized product of the target nucleic acid and the oligonucleotide, and
B. detecting the hybridized product as an indication of the presence of the target nucleic acid in the specimen.

This invention is also a method for the amplification and detection of a target nucleic acid comprising:

A. amplifying a target nucleic acid,
B. contacting the amplified target nucleic acid with the element described above wherein the oligonucleotide of the disposed nucleic acid reagent is complementary to a nucleic acid sequence of the target nucleic acid, to form an immobilized hybridized product of the amplified target nucleic acid and the nucleic acid reagent on the element, and
C. detecting the presence of the immobilized hybridized product as an indication of the presence of the target nucleic acid.

The present invention provides a method useful for the detection of nucleic acids. High signal and low background are features of the improved method. It is particularly useful for the detection of nucleic acids which are present in very low quantities, for example, as low as 100 molecules, in a specimen. This invention utilizes an improved element for diagnostic se whereby the capture probe is deposited in defined areas and is not easily dislodged by fluids or mechanical handling. Thus, the potential signal from the capture of the target nucleic acid is well defined and exhibits high density.

These features are achieved with a method using an element which has the appropriate nucleic acid reagent firmly attached to a solid support in the element. The disadvantages associated with reagent fusing and drying are avoided, and the reagents are not washed away during an assay.

The element provides these important advantages as a result of the use of a particular combination of polymeric particles and a polymeric adhesive to attach the particulate nucleic acid reagent to a solid sealable support. The amount of adhesive used is adjusted in relation to the amount of reagent present so the reagent and target nucleic acid can readily come into contact. The reagent has particularly small particles in order to provide high sensitivity and optimum adhesion to the support.

BRIEF DESCRIPTION OF THE DRAWINGS

The FIGURE is a graphical representation of the results of comparative assays performed as described in Example 2 below.

DETAILS OF THE INVENTION

Figure 1:
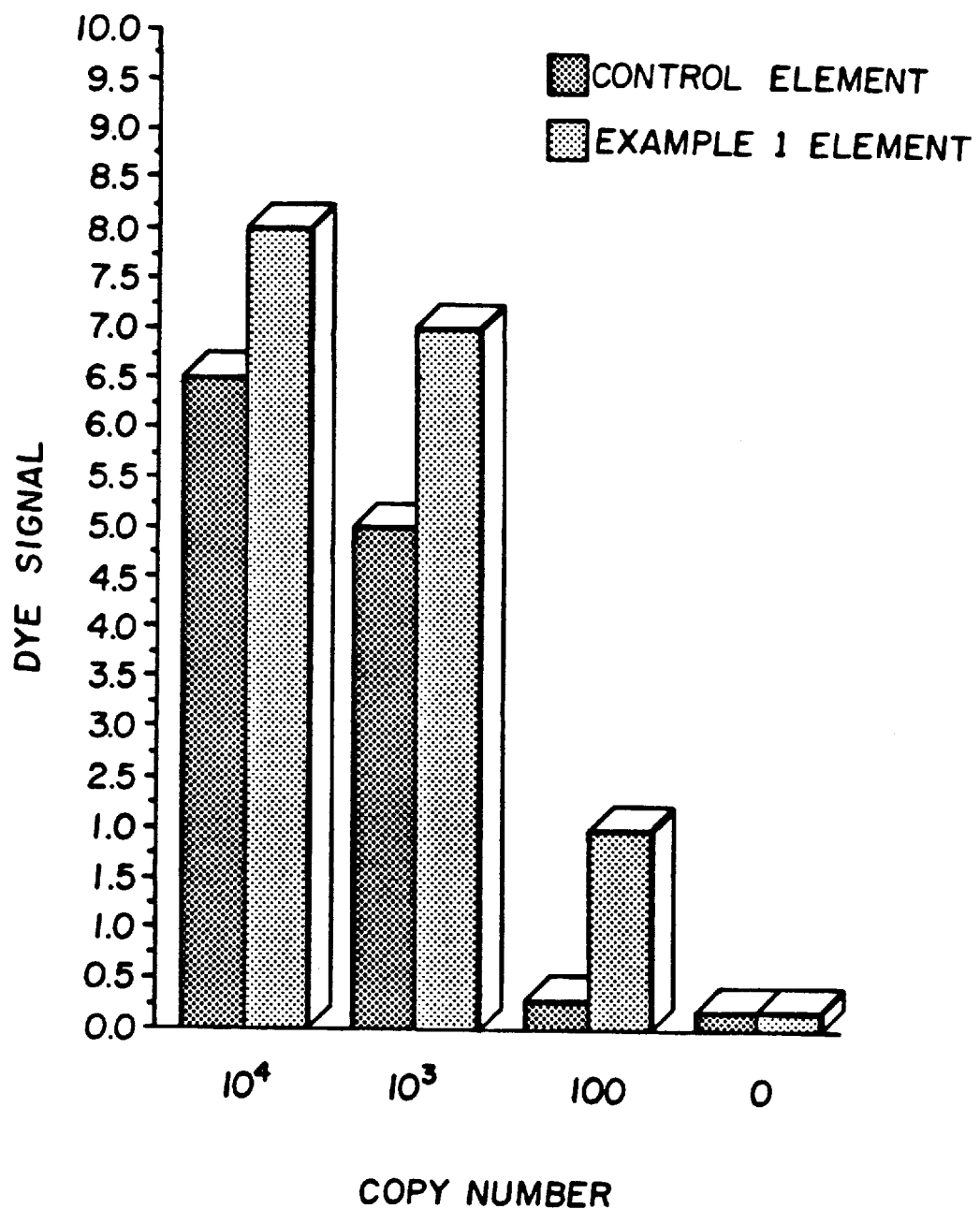

The element useful in this invention comprises a sealable support having disposed thereon (as described below) one or more nucleic acid compositions, each comprising a nucleic acid reagent in admixture with a water insoluble adhesive.

Sealable supports are resinous materials (usually synthetic polymers) which are capable of being sealed (or fused) to themselves or to another sheet of material using heat or ultrasonic pressure sealing techniques. Preferably, the supports are heat-sealable. Useful sealable supports include, but are not limited to, sheets, fibrous mats, and membranes which can be sealed to themselves in an appropriate manner and in appropriate places to provide channels or voids between sealed sheets, mats or membranes. It is also preferred that the support surface be roughened in some fashion to facilitate adhesion of the nucleic acid composition.

The supports can be composed of, for example, polyesters {such as poly(ethylene terephthlate), poly[4,4'-(hexahydro-4,7-methanoindan-5-ylidene)diphenylene terephthlate] and poly(4,4'-isopropylidenediphenylene 1,1,3-trimethyl-3-phenyl-5,4'-indandicarboxylate)}, polycarbonates [such as biphenol A polycarbonate (for example, LEXAN™ sold by General Electric)], polyamides [such as poly(p-phenylene terephthalamide)], polyimides [such as the polyimide product of 4,4'-diaminodiphenylether and pyromellitic dianhydride], and celluloses [such as cellulose acetate, and cellulose acetate butyrate].

In one embodiment described in U.S. Ser. No. 639,454 (noted above), sheets of polyethylene are sealed at the peripheral edges to form a container having voids for various reagents, including the nucleic acid reagents described herein. In another embodiment, laminates of polyethylene and a polyester, such as poly(ethylene terephthalate), can be heat sealed. Laminates can have a variety of layers therein including adhesives, vapor barriers or ultraviolet light blocking layers as well as sealable layers. Other embodiments would be readily apparent to one skilled in the art.

The nucleic acid reagent described herein is deposited on a surface of the sealable support, uniformly thereover, or in one or more defined regions. Preferably, the reagent is in a defined region of the support surface such as in a round spot, printed stripe or other desired configuration. In one embodiment, several different nucleic acid reagents are deposited in separate defined regions of the support surface so that a multiplicity of target nucleic acids can be simultaneously detected using the element. For example, the element can have a series of reagent spots or stripes.

The nucleic acid reagent useful in this invention is composed of particles of a first polymer (or composite of polymers) having a glass transition temperature ($T_{g1}$) of at least about 70° C. Preferably, the $T_{g1}$ is from about 70° to about 175° C., and more preferably it is in the range of from about 75° to about 140° C. Glass transition temperature refers to the temperature at which the polymer changes from a glassy state to a rubbery, flowing or tacky polymer. Procedures for measuring glass transition temperatures are described in *Techniques and Methods of Polymer Evaluation*, Vol. 1, Marcel Dekker, Inc., New York, 1966.

The particles useful herein are also impermeable and non-swellable in aqueous fluids. These properties insure structural integrity for the composition disposed on the sealable support of the element. Non-swellability refers to particles exhibiting little swell (that is, less than 10% swell) in an aqueous fluid as measured using a swellometer of the type described by Green et al, *J.Photo.Sci.*, 20, 205 (1972), after immersion of the particles in an aqueous fluid at 38° C. for about 2.5 minutes.

Preferably, the particles are spherical in shape although other shapes can be used as well as long as the largest dimension of the particles is no greater than the maximum diameter for spherical particles as described below. It is also preferred that the particles be substantially uniform in size. Critically, the largest particle dimension (for example, diameter) is from about 0.1 to about 3 μm, but a diameter in the range of from about 0.5 to about 2 μm is preferred.

The particles are generally composed of, at least on the surface thereof, naturally occurring or synthetic materials to which an oligonucleotide can be covalently attached (described below). Such materials generally have reactive groups with which the oligonucleotide or a derivatized form thereof can be reacted to form a covalent bond.

In general, any reactive group with which an amino or sulfhydryl group is reactive is useful in this context. Particularly useful reactive groups include, but are not limited to, an active halogen, carboxy, amidine, activated 2-substituted ethylsulfonyl, activated 2-substituted ethylcarbonyl, vinylsulfonyl, vinylcarbonyl, epoxy, aldehyde, sulfhydryl, amino (after activation), hydrazine and active esters such as succinimidoxycarbonyl. Preferred particles are organopolymeric beads such as those described in EP-A-0 323 692 (published Jul. 12, 1989) prepared from one or more ethylenically unsaturated polymerizable monomers having an active halogen, activated 2-substituted ethylsulfonyl or vinylsulfonyl groups. Most preferred particles have reactive carboxy groups, as described in copending U.S. Ser. No. 654,112 (filed Feb. 12, 1991 by Ponticello et al) which is a CIP of U.S. Ser. No. 539,768 (filed Jun. 18, 1990) which are prepared from monomers having the general structure

wherein R is hydrogen, halo or alkyl of 1 to 3 carbon atoms, M is hydrogen, an alkali metal ion or an ammonium ion and L is an organic linking group having from 8 to 50 carbon, oxygen, nitrogen or sulfur atoms in the linking chain.

Representative useful ethylenically unsaturated polymerizable monomers having reactive groups include, but are not limited to, acrylic acid, methacrylic acid, m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonylmethyl)phenyl]acrylamide, N-[2-(2-chloroethylsulfonyl)ethylformamidomethyl]acrylamide, mono-m & p-vinylbenzyl glutarate, mono-p-vinylbenzyl glutarate, mono-2-methacryloyloxyethyl glutarate, 2-(4-carboxybutyr-amido)ethyl methacrylate, 2-[N'-(5-carboxypentyl)-ureido]ethyl methacrylate, mono-methacryloylpenta-(oxyethylene) glutarate, mono-(4-acryloyloxybutyl) glutarate, 4-(4-carboxybutyramido) styrene, mono-2-(p-vinylbenzylthio)ethyl glutarate, mono-2-(m & p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)-propionic acid, 4-[2-(4-carboxybutyramido)ethylthiomethyl]styrene, 4-[2-(carboxymethoxyacetamido)-ethylthiomethyl]styrene, 4-[2-(carboxymethylthioacetamido)ethylthiomethyl]styrene, mono-2-(p-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-methacryloylpenta(oxyethylene) phthalate, mono-2-[2-{2-[4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio] benzylthio}butyric acid.

The monomers just described can be polymerized as homopolymers, but preferably they are copolymerized with one or more other ethylenically unsaturated polymerizable monomers.

More particularly, the particles useful in this invention are composed, at least on the surface thereof, of a polymer comprising:

(a) from about 0.1 to about 60 weight percent of recurring units derived from one or more ethylenically unsaturated polymerizable monomers having a reactive group as defined above, (b) from about 40 to about 99.9 weight percent of recurring units derived from one or more ethylenically unsaturated polymerizable monomers which, when homopolymerized, provide a water-insoluble homopolymer, and (c) from 0 to about 15 weight percent of recurring units derived from one or more ethylenically unsaturated polymerizable monomers other than those defined for components (a) and (b) above, including but not limited to hydrophilic monomers which provide colloidal stability to the copolymer.

Useful monomers for component (b) noted above include, but are not limited to, vinyl aromatics (for example, styrene and styrene derivatives such as 4-vinyltoluene, a-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, vinylidene chloride and crosslinkable monomers having two or more polymerizable groups (such as vinyl groups, for example divinylbenzene, and di- and triacrylates). Other monomers which are capable of providing a water-insoluble homopolymer would also be useful, and would be readily apparent to one skilled in the art. The vinyl aromatic monomers are preferred for component (b).

Useful monomers for component (c) include, but are not limited to, nonionic hydrophilic monomers such as acrylamide, methacylamide, N-isopropylacrylamide, 2-hydroxyethyl acrylate, 2-hydroxyethyl methacrylate, N-vinyl-2-pyrrolidone and others readily apparent to one skilled in the art. In addition, monomers having active methylene groups, such as 2-acetoacetoxyethyl methacrylate, and cationic monomers, such as N,N,N-trimethyl-N-vinylbenzylammonium chloride and 3-hydroxyethyl-1-vinylimidazolium chloride could be used.

Still other useful monomers for component (c) include those having polyoxyalkylene side chains as described for example in U.S. Pat. No. 5,086,143 (Sutton et al). Representative monomers, include but are not limited to, pentaethylene glycol monomethacrylate, decaethylene glycol monomethacrylate, eicosaethylene glycol monomethacrylate, pentaethylene glycol monoacrylate, polypropylene glycol monomethacrylate and polypropylene glycol monomethacrylate.

A preferred monomer for component (c) is 2-acetoacetoxyethyl methacrylate.

Mixtures of various monomers for each component (a), (b) and (c) can be copolymerized as long as the monomers are compatible with each other and sufficient reactive groups are present on the surface of the resulting particles.

Preferred first addition polymers include poly[styrene-co-mono-3-(p-vinylbenzylthio)propionic acid] or poly[styrene-co-mono-2-(p-vinylbenzylthio)ethyl succinate].

Preferably, the particles are composed of recurring units derived by addition polymerization from about 2 to about 15 weight percent of component (a), from about 85 to about 98 weight percent of component (b), and from 0 to about 10 weight percent of component (c). More preferably, they are composed of recurring units derived from about 2 to about 10 weight percent of (a), from about 90 to about 98 weight percent of component (b), and from 0 to about 10 weight percent of component (c).

The copolymers useful herein to make the particles are prepared using standard emulsion or suspension polymerization techniques, as described for example by Sorenson et al in *Preparative Methods of Polymer Science*, 2nd Edition (1968), Wiley & Sons, New York, and Stevens, *Polymer Chemistry, An Introduction*, Addison Wesley Publishing Co., London (1975).

The particles can also be core/shell particles having the noted polymer described above as the shell so that reactive groups are available on the surface. Core/shell particles and procedures for making them are well known, as described for example in U.S. Pat. No. 4,401,765 (Craig et al) and U.S. Pat. No. 4,997,772 (Sutton et al). The core of such particles can be composed of any suitable polymer which contributes to the requisite physical integrity and glass transition temperature and is generally different from that of the shell polymer.

Molecules of an oligonucleotide are covalently attached to the particles. The term "oligonucleotide" refers to a molecule comprised of two or more (preferably more than three) deoxyribonucleotides or ribonucleotides. Its size will depend upon many factors including the target nucleic acid to which it is complementary, the size of the polymeric particle to which it is attached, and the means of attachment to the particles including the length of any spacer molecule. Oligonucleotides can be prepared using methods known in the art and conventional synthesizers as described, for example in U.S. Pat. No. 4,965,188 (noted above) and U.S. Pat. No. 4,725,677 (Koster et al).

The oligonucleotide is covalently attached to the polymeric particles using any suitable technique. They can be directly attached by reacting the reactive groups on the surface of the particles with corresponding sulfhydryl, carboxy or amino groups of the oligonucleotide. Alternatively, the oligonucleotide can be biotinylated or otherwise modified to add a specific binding species which can then specifically bind with its corresponding receptor which can be attached to the particles. Avidin-biotin complexes are known to be used for this purpose as described for example in EP-A-0 139 489 (published May 2, 1985), EP-A-0 192 168 (published Aug. 27, 1986) and EP-A-0 370 694 (published Jul. 24, 1991). Incorporating biotin into an oligonucleotide can be achieved using known technology including that described in EP-A-0 097 373 (published Jan. 4, 1984).

Preferably, however, it is desired to chemically modify the oligonucleotide in order to provide reactive groups therein or to provide "spacer" groups or "linker" groups to extend the oligonucleotide away from the surface of the particles. Techniques for doing this are well known, as described for example, in U.S. Pat. No. 4,914,210 (Levenson et al) and WO 89/11548 (published Nov. 30, 1989).

The oligonucleotide of the nucleic acid reagent is complementary to a specific nucleic acid sequence of a target nucleic acid. This target nucleic acid can be naturally occurring in a virus or cell of a particular organism or any other material containing endogenous or invasive DNA or RNA, or be synthetically prepared using conventional procedures (for example, phosphoramidite chemistry).

The coverage of oligonucleotide on the surface of the particles may vary depending upon the size of the particles, the chemical means of attachment, the length of the oligonucleotide, and the length of any spacer molecule.

A polymeric adhesive is used to affix the nucleic acid reagent of the nucleic acid composition to the sealable support of the element. It also acts to bond the reagent particles to each other. This adhesive comprises a second polymer which has a glass transition temperature ($T_{g2}$) which is at least about 30° C. less than the glass transition temperature ($T_{g1}$) of the first polymer of the particles. Preferably, $T_{g2}$ is from about 30° to about 120° C. less than $T_{g1}$. $T_{g2}$ is also less than about 900° C. More preferably, $T_{g2}$ is in the range of from about −50° to about +40° C.

The adhesive is insoluble in aqueous fluids commonly encountered in diagnostic and analytical methods. While it is not essential, it is also preferred that the adhesive be non-swellable in aqueous fluids.

More particularly, the second polymer is composed of:

(d) from about 55 to 100 weight percent of recurring units derived from one or more ethylenically unsaturated polymerizable monomers used in component (b) of the first polymer described above, (e) from 0 to about 45 weight percent of recurring units derived from one or more ethylenically unsaturated monomers which form a water soluble homopolymer, or which provide hydrophilicity from polar groups [such as primary, secondary and tertiary amines, hydroxy and poly(alkyleneoxy) groups], anionic groups [such as carboxylate, sulfonate, sulfate, phosphate and phosphonate], and cationic groups [such as trialkylammonium and trialkylphosphonium] and others readily apparent to one skilled in the art, and (f) from 0 to about 15 weight percent of recurring units derived from one or more ethylenically unsaturated monomers which provide crosslinking in the polymer adhesive.

While the monomers described above for component (b) of the first polymer are useful also in component (d), the preferred monomers for component (d) are alkyl acrylates and methacrylates wherein the alkyl group has from 1 to 8 carbon atoms (such as methyl, ethyl, n-propyl, n-butyl, isobutyl, 2-ethylhexyl, hexyl and octyl), and which alkyl group can also be interrupted with one or more: thio, oxy or iminoalkyl groups having 1 to 6 carbon atoms. More preferred monomers include, but are not limited to, methyl acrylate, methyl methacrylate, n-butyl acrylate and n-butyl methacrylate. Methyl acrylate is most preferred.

Useful monomers for component (e) include, but are not limited to, charged monomers (cationic or anionic) such as acids and salts thereof, including but not limited to, acrylic acid, methacrylic acid, itaconic acid, 2-acrylamido-2-methylpropanesulfonic acid, 3-methacryloyloxypropane-1-sulfonic acid and their salts, N-(2-acryloyloxyethyl-N,N,N-trimethylammonium methosulfate, 3-hydroxyethyl-1-vinylimidazolium chloride, 2-aminoethyl methacrylate hydrochloride, N-(2-aminopropyl)methacrylamide hydrochloride, 2-carboxyethyl acrylate, p-styrene sulfonic acid and salts thereof, m & p-carboxymethylstyrene and its salts, and other ethylenically unsaturated polymerizable sulfonates, carboxylates, sulfates, phosphonates, quaternary ammonium salts, pyridinium salts, imidazolium salts, quinoxalinium salts, and other salts readily apparent to one skilled in the art. Also useful are the carboxy-containing monomers (and salts thereof) described above for component (a) of the first polymer.

Nonionic monomers which also are useful in component (e) include, but are not limited to, amine-containing monomers, such as dimethylaminopropyl acrylate and diethylaminoethyl methacrylate and hydroxy-containing monomers such as 2-hydroxyethyl acrylate, 2-hydroxyethyl methacrylate, 2,3-dihydroxypropyl acrylate, pentaethylene glycol monoacrylate and others readily apparent to one skilled in the art.

Preferred monomers in component (e) include 2-acrylamido-2-methylpropanesulfonic acid and salts thereof, 2-aminoethyl methacrylate hydrochloride and N-(2-aminopropyl)methacrylamide hydrochloride.

The monomers for component (f) which provide crosslinking can either be crosslinked during polymerization, or provide crosslinking after subsequent chemical reaction with themselves or with additional crosslinking agents. Such monomers include multifunctional vinyl monomers such as di- and triacrylates and methacrylates (such as ethylene diacrylate and ethylene dimethacrylate), divinylbenzenes, and monomers containing active methylene groups which can be crosslinked using known chemical reactions. Examples of the latter include 2-acetoacetoxyethyl methacrylate, N-(2-acetoacetoxyethyl) acrylamide, N-(2-acetoacetamidoethyl)methacrylamide, 6-(m & p-vinylphenyl)-2,4-hexanedione, ethyl acryloylacetate and others known in the art, such as those described in U.S. Pat. No. 3,554,987 (Smith), U.S. Pat. No. 3,459,790 (Smith) and U.S. Pat. No. 4,247,673 (Ponticello et al).

Preferred monomers for component (f) include 2-acetoacetoxyethyl methacrylate, N-(2-acetoacetoxyethyl) acrylamide and N-(2-acetoacetamidoethyl)methacrylamide.

Preferably, the copolymers useful in preparing the adhesive are composed of recurring units derived from about 70 to about 98 weight percent of component (d), from about 2 to about 30 weight percent of component (e), and from 0 to about 10 weight percent of component (f). More preferably, they are composed of recurring units derived from about 85 to about 95 weight percent of component (d), from about 2 to about 15 weight percent of component (e), and from 0 to about 8 weight percent of component (f).

A preferred addition polymer for the adhesive is poly [methyl acrylate-co-2-acrylamido-2-methylpropanesulfonic acid, sodium salt-co-2-acetoacetoxyethyl methacrylate].

The polymers useful as adhesives can be prepared using conventional emulsion polymerization techniques, for example as described in the literature cited above for preparation of the first polymer.

In the nucleic acid reagent composition comprising a mixture of polymeric adhesive and nucleic acid reagent used in this invention, the adhesive can be present in an amount of up to about 20% by dry weight. Preferably, the adhesive is present in an amount of from about 1 to about 20% by weight, with an amount of from about 2 to about 10 weight percent being more preferred.

The composition can optionally contain other addenda, such as buffers, surfactants or binders in minor amounts, that is generally less than about 5% of the total composition weight.

The nucleic acid reagent composition can be applied to the sealable support in any suitable manner. For example, it can be coated thereon using standard coating equipment and techniques, applied by hand, printed thereon, spotted with a pipette tip, microsyringe tip or microdispensing pump, and then dried. Preferably, however, the composition is merely disposed in an aqueous suspension with a microsyringe tip and dried on a sealable support. Drying is accomplished by heating the disposed composition in a range of from about 10° to about 80° C. less than the glass transition temperature of the first polymer described above.

The coverage of the nucleic acid reagent composition on the support can be varied considerably depending upon the type of assay format, the configuration of the assay element and other factors that one skilled in the art would readily perceive. For example, the composition can be applied uniformly to the sealable support, or applied in defined regions thereof (as noted above). Application of the composition in defined regions is preferred. Techniques for applying different reagents to different regions are well known. In some instances, the reagents can be disposed in defined regions that provide visual patterns for easy detection.

It is preferred to use a sealable support which has been pretreated to render it more hydrophilic. The nucleic acid reagent composition is adhered more effectively to the support in such embodiments. The pretreatments can be of a chemical, electrical or mechanical nature, or a combination of different types of treatments. For example, chemical treatments include the use of chromic acid which involves etching a surface with sodium dichromate in sulfuric acid for a few minutes.

The support can also be treated with activated species in gases, such as noble gases, as described for example in U.S. Pat. No. 3,526,583 (Hayward) and by Hanson et al, *Chem.&Ena.News*, 44, pages 58–59, Sep. 26, 1966. Still another known procedure is the use of nitrous oxide at elevated temperatures.

Electrical treatments include corona discharge, flaming and electrode discharge processes which are also well known in the art, for example as described in *Adhesive Bonding*, Lee (Ed.), Plenum Press, New York, pages 265–267.

Another pretreatment involves simultaneous chemical and electrical treatment such as with a radio frequency electromagnetic field in the presence of a reactive gas. Details of such procedures are provided for example in U.S. Pat. No. 3,761,229 (Lidel) and U.S. Pat. No. 4,072,769 (Lidel).

While other chemical, electrical and mechanical pretreatments would be readily apparent to one skilled in the art, preferred pretreatments include corona discharge treatment, chromic acid treatment and treatment with a radio frequency electromagnetic field in the presence of a reactive gas. Corona discharge treatment is most preferred.

Alternative or supplemental to the pretreatments described above, the support can be pretreated by applying a hydrophilic polymer thereto which acts as a hydrophilic subbing layer and which improves adhesion of the disposed composition described above. Subbing layer polymers and methods for their preparation are well known in the art, for example as described in U.S. Pat. No. 3,143,421 (Nadeau et al) and U.S. Pat. No. 3,201,249 (Pierce et al). Generally, such polymers are composed of recurring units having one or more pendant anionic or hydrophilic groups such as carboxy, sulfonyl, phosphono, phosphinyl, carbonyl and hydroxy. Other general characteristics of such polymers include, but are not limited to, the presence of some halogen content from monomers such as vinyl chloride, vinylidene dichloride and others readily apparent to one skilled in the art.

Particularly useful subbing layer materials include poly (acrylonitrile-co-vinylidene chloride-co-acrylic acid), poly (methyl acrylate-co-vinylidene chloride-c-itaconic acid), poly(monomethyl itaconate-co-vinylidene chloride), poly (monoethyl itaconate-co-vinylidene chloride) and poly (monobutyl itaconate-co-vinylidene chloride).

The subbing layer materials are generally applied to the sealable support in any suitable fashion such as coating, dipping, spotting or spraying using known procedures. The subbing layer can be applied over the entire support surface, or to defined regions thereof.

The element can be prepared by disposing the nucleic acid reagent composition on a sealable support as defined herein, and heating the disposed composition at a temperature and for a time sufficient to dry the composition. While the time and temperature for suitable adhesion can be varied inversely, in general, a temperature in the range of from about 10° to about 80° C. less than the glass transition temperature of the first polymer is used. The time for heating is generally from about 10 to about 40 seconds.

The element can be used in the analytical method of this invention as described in more detail below and in a number of formats. For example, the element can be merely a simple article which is used in a laboratory or doctor's office with standard pipettes, beakers and other equipment known for such assays, including a suitable container in which the assay is carried out. The most crude container would be a test tube, cuvette, flask or beaker, but more sophisticated containers have been fashioned in order to facilitate automated procedures for performing the method.

Alternatively, the element can be incorporated and used as part of a disposable test device, of which many configurations are known in the art including, but not limited to those described in U.S. Pat. No. 3,825,410 (Bagshawe), U.S. Pat. No. 3,888,629 (Bagshawe), U.S. Pat. No. 3,970,429 (Updike), U.S. Pat. No. 4,446,232 (Liotta), U.S. Pat. No. 4,833,087 (Hinckley), U.S. Pat. No. 4,923,680 (Nelson), U.S. Pat. No. 4,921,677 (Hinckley et al) and EP-A-0 408 738 (published Jan. 23, 1991).

A preferred container for incorporation of the element is a self-contained test device like those described, for example, in U.S. Ser. No. 639,454 (noted above) and U.S. Ser. No. 673,053 (filed Mar. 21, 1991 by Schnipelsky et al) and EP-A-0 381 501 (published Jun. 5, 1991). Such test devices are also known in the art as chemical test packs, pouches or cuvettes. They are constructed to provide certain temperature characteristics during the practice of the method as described in U.S. Pat. No. 4,902,624 (to Columbus et al). Such test devices have a multiplicity of reaction chambers (or "blisters" as they are often called) having various reagents, buffers and other materials which are useful at various stages in the assay. The test devices can be appropriately and rapidly heated and cooled in cycles to promote the various steps of PCR amplification, a preferred method of this invention. Other useful containers could be suitably fashioned for automated or single use of the method of this invention.

In such test devices, the element is disposed in a particular chamber (or "blister") through which reagents and fluids are passed in order to facilitate a sequence of reactions in order to obtain detection of the target nucleic acid. In this instance, the reagents and fluids are considered to "flow by" the immobilized nucleic acid reagent on the element. The nucleic acid reagent on the element is used to "capture" the target nucleic acid for detection. The element can be incorporated into the test device by affixing it with adhesives, fusing the element to a polymeric wall of the test device or using other conventional means. In another embodiment, the element itself can form a wall or integral portion of the test device.

The test device can be self-contained, meaning that, while it has means for cooperating with outside sources of pressure for liquid transfer, it is constructed to be completely closed after a sample has been introduced so that no leakage can occur.

In a preferred embodiment, the test device comprises two relatively thin sheets of flexible polymeric material [such as a heat- or pressure-sealable polyethylene-poly(ethylene terephthalate) laminate, for example SCOTCHPAK™ heat-sealable film No. 229 or No. 241 both available from 3M Corporation] which are secured along their outer edges using heat or ultrasonic pressure-sealing. A heat-activatable adhesive, such as copolyesters of ethylene glycol, diethylene glycol and terephthalic acid as described in U.S. Pat. No. 4,352,925 (Petke et al), or a mixture of a polystyrene-polyisoprene-polystyrene block copolymer and a poly (ethylene-co-vinyl acetate) as described in U.S. Pat. No. 4,126,464 (Dann) can be used also.

Chambers or channels are formed between the sheets by sealing the sheets at certain points so that reagents and fluids can be kept within the test device and moved therethrough using pressure devices. Within one such chamber is located the element. Preferably, the element is located in a chamber which is designed in a relationship with the other compartments and passageways so that the reagents and fluids used in the method, flow by the element and into a storage chamber designated to collect waste reagents and fluids.

One preferred test device useful in the practice of this invention is described in commonly assigned and copending U.S. Ser. No. 979,569, filed on the same day as the present application by Chen, Findlay, Atwood and Bergmeyer, the copending application being entitled "Nucleic Acid Material Amplification and Detection Without Washing". This device generally has a reaction compartment which contains reagents needed for amplification of a target nucleic acid, a detection site containing the element described herein, and storage compartments containing signal generating reagents or composition and wash solution, and passageways connecting the compartments to the detection site. A method of amplification of a target nucleic acid is also described therein whereby less wash steps are used.

The element described herein can be used in a wide variety of methods for the detection of a target nucleic acid. It is particularly useful for the amplification and detection of one or more specific nucleic acid sequences present in one or more target nucleic acids in a test specimen. Such specimens can include cellular or viral material, hair, body fluids or other materials containing genetic DNA or RNA which can be detected.

The present invention is especially useful for producing, in exponential quantities relative to the number of reaction steps involved, at least one specific nucleic acid sequence of an infectious agent. The product will be a discrete nucleic acid duplex with termini corresponding to the ends of the specific primers employed. Any source of nucleic acid, purified or not, can be utilized as the starting material. A mixture of nucleic acids can be employed if desired. The sequence to be duplicated can be a fragment of the entire nucleic acid. Moreover, a plurality of double stranded nucleic acids can be amplified and detected simultaneously by using a corresponding set of primers and detection means (including capture reagents described above) for each specific nucleic acid. Multiple sequences in the same nucleic acid can also be amplified and detected.

Nucleic acids to be detected can be obtained from various sources including plasmids, naturally occurring DNA or RNA from any source. It may be extracted from various tissues including blood, peripheral blood mononuclear cells (PBMC), tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or viral infected cells.

The method described herein can be used to provide the detection or characterization of specific nucleic acid sequences associated with infectious diseases, genetic disorders or cellular disorders such as cancers. It may also be used in forensic investigations and DNA typing. For purposes of this invention, genetic diseases include specific deletions or mutations in genomic DNA from any organism, such as sickle cell anemia, cystic fibrosis, α-thalassemia, β-thalassemia and others readily apparent to one skilled in the art. Human Leukocyte Antigen (HLA) can be categorized with the present invention. Bacteria which can be detected include, but are not limited to, Salmonella, Streptococcal organisms, Chlamydial organisms, Gonococcal organisms, *Mycobacterium tuberculosis, Mycobacterium avium* complex, *Mycoplasma Haemophilus influenzae*, Shigella and Listeria. Viruses which are detectable include, but are not limited to, herpes, Epstein Barr virus, cytomegalovirus, human papilloma virus, hepatitis and retroviruses such as HTLV-I, HTLV-II, HIV-I and HIV-II. Protozoan parasites, yeasts and molds are also detectable. Other detectable species would be readily apparent to one skilled in the art. Detection of DNA associated with HIV-I (and other retroviruses), cytomegalovirus or human papilloma virus is advantageously accomplished with this invention. Most preferably, it is used to detect DNA associated with retroviruses, such as HIV-I.

In one embodiment, the element is used to provide a capture probe in what is known as a hybridization assay. Details of hybridization assays, procedures and reagents useful therein are described in such references as U.S. Pat. No. 4,358,535 (to Falkow et al), U.S. Pat. No. 4,486,539 (Ranki et al) and U.S. Pat. No. 4,925,785 (noted above). The captured target nucleic acid can be suitably detected using a water-soluble oligonucleotide (or detection probe) which can directly or indirectly hybridize with the target (either before, during or after capture).

The elements are also useful for "capturing" amplified targeted nucleic acids following polymerase chain reaction (or PCR). The details of PCR are also widely known, for example in such references as those mentioned in the Background above, and further in EP-A-0 408 738 (noted above) and U.S. Ser. No. 693,574 (filed Apr. 30, 1991 by Findlay et al). Detection probes useful in the practice of this invention can be hybridized directly or indirectly to the targeted nucleic acid. By "indirectly" is meant that there may be intermediate oligonucleotides which are complementary to both, the target nucleic acid and the detection probe. Procedures for attaching labels and preparing probes are well known in the art, for example, as described by Agrawal et al, *Nucleic Acid Res.*, 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels include radioisotopes, electron-dense reagents, chromogens, fluorogens, phosphorescent moieties, ferritin and other magnetic particles (U.S. Pat. No. 4,795,698 of Owen et al and U.S. Pat. No. 4,920,061 of Poynton et al), biotin and other specific binding moieties, chemiluminescent moieties and enzymes (see for example, U.S. Pat. No. 4,707,440 of Stavrianopoulos). Useful enzymes include, but are not limited to, glucose oxidase, peroxidases, uricase, β-galactosidase, glycosylase and alkaline phosphatase, and can be attached to oligonucleotides using known procedures. Substrates and dye forming compositions for such enzymes are well known, for example as taught in U.S. Pat. No. 4,994,373 (Stavrianopoulos et al).

Where the label is a more preferred enzyme such as a peroxidase, at some time during the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747 of Bruschi), or other compounds which react to provide a dye in the presence of peroxidase and hydrogen peroxide. Useful dye-providing compositions are described in U.S. Pat. No. 5,024,935 (McClune et al) and shown in the examples below.

Particularly useful dye-providing compositions provide a chemiluminescent or colorimetric signal in response to a peroxidase label, and include one or more water insoluble macromolecular weight materials which exhibit shear thinning immediately upon the application of only very little, shearing force or agitation. The concept of "shear thinning" (also known as "pseudoplasticity" or "pseudoplastic behavior") is described in more detail by Alger, *Polymer Science Dictionary*, Elsevier Science Publishers, Ltd., 1990, pages 436–7. Thus, "shear-thinning" is known as non-Newtonian flow in which the apparent viscosity decreases with increasing shear rate.

The materials which are useful in the practice of the present invention are those which exhibit "shear thinning" to a viscosity of 1 poise at a shear rate less than 100/second, as observed at a temperature less than about 50° C. In this definition, shear thinning means that at least about 60% (and preferably at least 80%) of the descrease in viscosity with increasing shear rate, occurs at less than about 100/second. These materials gel quickly when cooled and unagitated, form transparent gels through which a calorimetric or chemiluminescent signal can be determined (visual or instrument evaluation) and are easily squeezed through narrow channels as a result of their shear thinning property. Useful macromolecular weight materials include, but are not limited to agarose, non-crosslinked polyacrylamides, block copolymers of polyethylene and polypropylene (such as the PLURONIC™ surfactants available from BASF Corporation) and chill gelable microgels that are described in more detail in Canadian 1,240,445.

Agarose, as the preferred material in the practice of this invention, is generally present in the dye-providing composition in an amount of from about 0.1 to about 3 weight percent. Preferably, it is present in an amount of from about 0.25 to about 1.5 weight percent. The useful amounts of other macromolecular materials will vary depending upon the type of material used, but can be readily determined by a skilled worker.

Detection of the presence of the label on the capture probe can be achieved using suitable detection equipment and procedures which are well known. Certain signals may be visible to the eye without the use of detection equipment.

In an alternative and preferred embodiment, a primer of the PCR process is biotinylated and the amplified nucleic acid is detected using detectably labeled avidin or a derivative thereof. For example, avidin can be conjugated with an enzyme, or have a radioactive moiety or another detection moiety like those described for the detection probes noted above. Biotin on the amplified product complexes with the avidin, and appropriate detection reagents and techniques are used. Biotinylation of primers can be carried out using known procedures such as those described in U.S. Pat. No. 4,962,029 and U.S. Pat. No. 4,707,440 (both noted above).

The element useful in this invention can be included in a diagnostic kit which also contains one or more reagents, equipment or instruction sheets for using the element. Preferably, the kit includes a detection reagent for detecting the hybridization product of the nucleic acid reagent oligonucleotide and target nucleic acid in the element and the target nucleic acid (either with or without PCR). By "detection reagent" is meant one or more individual reactive materials which can singly or collectively provide a detectable signal. Most preferably, the detection reagent is a biotinylated primer used in PCR which is complementary to the target nucleic acid. Alternatively, the detection reagent is a water soluble, labeled oligonucleotide useful in a hybridization assay.

The kit can include other reagents and fluids such as, but not limited to, wash solutions, extraction compositions, signal-producing reagents, diluents, buffers, primers, probes, DNA polymerases and PCR reagent compositions. The kit components are generally packaged individually in a suitable manner for transport and storage under the appropriate conditions.

Although this disclosure has focused on the use of polymerase chain reaction, the invention is also useful with other procedures for replication and amplification of nucleic acids, including but not limited to, transcription based amplification techniques as described by Kwoh et al *Proc.Nat'l.Acad.Sci.USA* 87, page 1974, 1989. nucleic acid ligase techniques described by Wu et al *Genomics*, 4, page 560, 1989 and Barringer et al *Gene*, 89, page 117, 1990, and ribonuclease H cleavage of DNA-RNA probes annealed to nucleic acid targets.

The following examples are included to illustrate the practice of this invention, and are not meant to be limiting in any way. All percentages are by weight unless otherwise noted.

Materials and Methods for Examples:

A nucleic acid reagent used in Examples 1 and 2 was prepared as follows:

Polymeric particles (1.2 μm average diameter) of poly [styrene-co-mono-2-(p-vinylbenzylthio)ethyl succinate]

(95:5 weight ratio) were prepared using known emulsion polymerization techniques. To these particles were attached molecules of the oligonucleotide:

SEQ ID NO:1:

5'-X-GAGACCATCA ATGAGGAAGC TGCAGAAT-3'
wherein x is an aminediol linking group with two tetraethylene glycol spacer groups prepared and attached to the oligonucleotide according to the teaching of U.S. Pat. No. 4,962,029 (noted above).

The oligonucleotide molecules were attached to the particles to form a nucleic acid reagent as follows:

The particles were washed twice with 2-(N-morpholino) ethanesulfonic acid buffer (0.1 molar, pH 6). Samples (30 µg) of the particles suspended in the buffer (1 ml) were mixed with 1-(3-dimethylaminopropyl)-3-ethylcarbodiimide hydrochloride (0.15 ml of 100 mg/ml of buffer) and the oligonucleotide (0.0288 ml of 57.3 OD/ml of purified water, 1.65 OD units or 55 µg). The mixture was rotated end over end at room temperature (20°–25° C.) for 15 hours and centrifuged. The particles were washed three times with water and resuspended in purified water at a solids content of 0.9%.

The nucleic acid reagent was mixed with an adhesive of poly(methyl acrylate-co-2-acrylamido-2-methylpropanesulfonic acid, sodium salt-co-2-acetoacetoxyethyl methacrylate) (90:4:6 weight ratio). The resulting composition comprised about 18% (dry weight) of adhesive. This mixture, in aqueous suspension, was applied to a heat-sealable support to form an element as described below in Example 1.

Primers used in the PCR process of Example 2 were as follows:

SEQ ID NO:2:

5'-X-AGTGGGGGGA CATCAAGCAG CCATGCAA-3'

SEQ ID NO:3:

5'-TTCCTGCTAT GTCACTTCCC CTTGGTTC-3'
wherein X represents a biotintetraethylene glycol spacer group prepared and attached to the oligonucleotide according to the teaching of U.S. Pat. No. 4,914,210 (noted above).

For Example 3, the nucleic acid reagent was similarly prepared using particles of poly[styrene-co-3-(p-vinylbenzylthio)propionic acid] (97.6:2.4 molar ratio) of different sizes, and the following oligonucleotide was similarly attached to the particles:

SEQ ID NO:4:

5'-ATTATCTTTT ATATTCTAAC CAGGATT-X-3'
wherein X comprises two tetraethylene glycol spacers and a 3-amino-1,2-propanediol linker at the 3' end.

Particles of poly[m & p-vinyltoluene (64:36)-co-methacrylic acid] (98:2 weight ratio) were also used in Example 3. These particles were prepared either using conventional suspension polymerization techniques or the limited coalescence procedures described in U.S. Pat. No. 3,615,972 (Morehouse, Jr. et al).

The target nucleic acid for Example 2 was a 140-nucleotide segment of the gap region of HIV-I.

A wash solution (250 µl) comprised a buffered solution of sodium phosphate (10 mmolar, pH 7.4), sodium chloride (150 mmolar), ethylenediaminetetra-acetic acid (1 mmolar) and decyl sulfate (1%). The wash solution was preheated to 55° C. for use.

The DNA polymerase used in the PCR was isolated from *Thermus aquaticus*.

A conjugate of streptavidin and horseradish peroxidase was obtained from Zymed Labs (San Francisco) and was diluted 1:8000 with casein (0.5%) in a phosphate buffer solution (pH 7.3) containing thimerosal preservative (0.01%).

A leuco dye composition for use in Example 2 was prepared as follows: 2-(4-hydroxy- 3,5-dimethoxyphenyl)-4,5-bis(4-methoxyphenyl)imidazole (to make a 0.1% solution) was dissolved in a solution of poly(vinyl pyrrolidone)(20%) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 µmolar) in sodium phosphate buffer to produce a final concentration of 1% poly (vinylpyrrolidone) and 0.005% leuco dye.

A leuco dye composition for use in Example 3 was prepared as follows: A solution of poly(vinylpyrrolidone) (25 g) in water (100 ml) was mixed with a solution of 4,5-bis(4-dimethylaminophenyl)-2-(4-hydroxy-3,5-dimethoxyphenyl)imidazole leuco dye (0.2 g) in N,N-dimethylformamide (1 ml) and stirred for 1 hour. The resulting dispersion was then added to a solution prepared by mixing monosodium phosphate, monohydrate (2.76 g) dissolved in water (1900 ml), diethylenetriaminepentaacetic acid solution (0.2 ml, 0.1 molar) and 4'-hydroxyacetanilide (1.51 g), and adjusting to pH 6.82 with a 50% sodium hydroxide solution. Hydrogen peroxide (2 ml, 30%) was added and the dispersion was stirred. Finally, the resulting leuco dye dispersion (24.75 ml) was mixed with dimedone (0.25 ml, 25 µmolar) and agarose (0.125 g) to form a leuco dye dispersion containing about 0.5% agarose. The dispersion was heated at about 80° C. until the agarose dissolved.

The PCR reaction solution for Example 2 comprised a solution of tris(hydroxymethyl)amino-methane buffer (10 mmolar, pH 8), potassium chloride (50 mmolar), magnesium chloride (10 mmolar) and gelatin (10 µg). To this solution were added the primers (100 pmoles of each), dNTP's (1.5 mmolar of each) and the DNA polymerase (7.5 units).

For Example 3, the following solutions were prepared to provide the PCR reagents:

A storage buffer for the DNA polymerase was prepared from tris(hydroxymethyl)aminomethane buffer (8 ml, 1 molar, pH 8), potassium chloride (13.32 ml, 3 molar), diethiothreitol (0.4 ml, 1 molar), ethylenediaminetetraacetic acid (0.16 ml, 0.25 molar), glycerol (250 ml, 80%), a surfactant solution (6.67 ml) containing 30% NONIDET™ P-40 nonionic surfactant (Sigma Chemical) and 30% TWEEN™ 20 nonionic surfactant (ICI Americas, Inc.) and a solution of gelatin (4 ml, 2%) so that the final concentrations were buffer (20 mmolar), potassium chloride (100 mmolar), dithiothreitol (1 mmolar), ethylenediaminetetraacetic acid (0.1 mmolar), glycerol (50%), surfactants (0.5% each), gelatin (200 µg/ml) and water to make 400 ml of solution.

A second buffer solution was also prepared to contain tris(hydroxymethyl)aminomethane (10 mmolar, pH 8.3), potassium chloride (50 mmolar), magnesium chloride (10 mmolar), gelatin (10 µg) and glycerol (7.5%).

A third buffer solution was prepared containing tris (hydroxymethyl)aminomethane (10 mmolar) and TWEEN™ 20 nonionic surfactant (0.5%).

The PCR reagent solution was then prepared from the above three buffer solutions by adding a mixture of 12 µl of the storage buffer to 288 µl of the second buffer solution, then to 220 µl of this mixture, adding 80 µl of the third buffer solution, and finally adding the biotinylated primers thereto to a concentration of 40 pmolar.

EXAMPLE 1

Preparation of Element

This example demonstrates the preparation of an element useful in this invention and compares it to an element outside the scope of this invention, that is, an element wherein the nucleic acid reagent is adhered to a support in another fashion.

An element useful in this invention was prepared using as a solid support a sample of Type 241 SCOTCH PAK™ laminate (3M Company) which is a laminate of polyethylene and polyethylene terephthalate. The polyethylene side of the laminate was corona treated to a level of 56–59 dynes/cm² using conventional treatment equipment obtained either from Pillar Technologies (Hartland, Wis.) or Enercon Industries (Menomonee, Wis.).

The polyethylene side of a sheet of polyethylene-poly(ethylene terephthalate) laminate was heat sealed over the element support to form an enclosed detection channel. This channel contained an inlet tip for injection of fluids into the channel and an outlet means to allow fluids to exit the channel.

The composition of adhesive and nucleic acid reagent described above was applied to the corona treated support in the form of an aqueous suspension (2 µl, 0.9% solids of reagent, 0.2% adhesive) in water. The suspension was applied in a defined region of the support in the detection channel and dried using a hot iron (95° C. for 30 seconds) in contact with the bottom of the support. The sheet of laminate was then heat sealed over the element to form an enclosed detection channel.

Before heat sealing the sheet of laminate over the element, a physical test was performed to determine how well the nucleic acid reagent composition was immobilized onto the support. This test comprised rubbing the dried deposit of composition, and folding the support 180 degrees. In the element of this invention, the reagent did not detach from the support but was firmly immobilized thereon. Very little composition came off the support during these physical tests.

A Control element was similarly prepared using the same support and nucleic acid reagent except that the adhesive was omitted. The nucleic acid reagent (0.9% solids suspension) in 1 µl glycine buffer (0.1 molar, pH 8.5) was applied to a defined region of the corona treated support, dried and a sheet of laminate was heat sealed over the deposit as described above. Before heat sealing, the dried reagent was physically rubbed and the support was bent 180 degrees to see how well the reagent adhered to the support. Much of the reagent detached from the support during these physical tests.

EXAMPLE 2
Use of Elements in PCR Method

This example demonstrates and compares the use of the elements described in Example 1 in the amplification and detection of a sequence of HIV-I DNA.

To the PCR reagent solution described above were added different amounts of the target HIV-I DNA fragment noted above (0, 100, 10³ and 10⁴ copies or molecules). The total volume of each of the resulting solutions was 100 µl.

Each solution was placed in 250 µl microfuge tubes and amplified using PCR through 40 cycles of the following protocol:

Denaturation: heat to 96° C. and hold for 30 seconds, and
Priming/extension: cool to 68° C. and hold for 1 minute.
The apparatus used for the PCR was a Perkin-Elmer Thermocycler commercially available from Cetus/Perkin Elmer.

After the last cycle, the solutions were heated to 95° C. and held for 5 minutes to denature the resulting double-stranded products. The heated solutions were each injected into the detection channel of the elements (Example 1 and Control) in a manner to insure uniform contact with the nucleic acid reagent immobilized therein. Following solution injection, each element was incubated at 42° C. for 5 minutes to allow hybridization of the complementary target nucleic acid to the oligonucleotide of the reagent in the element. Remaining fluid was removed either by forcing it out with compressed air, or by drawing it out using a syringe.

The wash solution described above was injected into each element twice to remove unhybridized materials. Once the wash fluid had been removed the last time, the solution containing the conjugate of streptavidin and peroxidase (200 µl) was injected into each element and incubated at 42° C. for two minutes. Once that solution was removed, the leuco dye solution (200 µl) was similarly injected followed by another incubation for five minutes.

The remaining fluid was removed, and the dye signal apparent in the element was visually graded on a scale of 0 to 10 (highest density). The results are shown in the FIGURE. The background (0 copy number) for both elements was quite low. However, for the assays of amplified target nucleic acid, the element of this invention provided higher signal at each concentration of target nucleic acid, indicating that the nucleic acid reagent was better retained in the element through the detection process with its repeated washes and contact with several different fluids. As noted above in Example 1, much of the reagent in a sample of the Control element was easily rubbed off the support, so it is believed that the fluids used in the assay removed it during the assay. It is quite important that the element of this invention demonstrated high sensitivity to the presence of a low concentration (100 copy number) of target nucleic acid.

EXAMPLE 3

Comparative Example Using Mixture of Different Sized Particles in Reagent Using Treated and Untreated Supports This example demonstrates the practice of this invention in preparing an element containing a nucleic acid reagent composition, and compares its use to the use of an element outside the scope of this invention. It also compares the use of treated supports to the use of untreated supports.

Poly[styrene-co-3-(p-vinylbenzylthio)-propionic acid] (mole ratio 97.6:2.4, weight ratio 95:5) aqueous polymer bead dispersions were prepared with different particle sizes, and an oligonucleotide identified below was covalently bound thereto using the procedures described in U.S. Ser. No. 654,112 (filed Feb. 12, 1991 by Ponticello et al) and in U.S. Ser. No. 539,774 (filed Jun. 18, 1990 by Sutton et al), respectively. The oligonucleotide had the sequence SEQ ID NO:4 shown above linked to the particle through two tetraethylene glycol spacers, a 3-amino-1,2-propanediol moiety, and a thymine base. The oligonucleotide was appended to the polymer particle through the amino group of the 3-amino-1,2-propanediol moiety to form reagents.

Reagents were prepared having different average particle sizes:

Reagents useful in the practice of this invention comprised particles having an average size of about 1.3 µm and were formulated at 2.0% solids with the polymeric adhesive described above (0.1% solids) in 2-amino-2-hydroxymethyl-1,3-propanediol/ethylenediamine tetraacetic acid buffer.

Nucleic acid reagents outside the scope of this invention (Control A) comprised particles having an average size of about 8 µm and were formulated at 4.0% solids with the polymeric adhesive (0.1% solids) in 2-amino-2-hydroxymethyl-1,3-propanediol/ethylene-diamine tetraacetic acid buffer. Controls B and C contained mixtures of particles with different sizes: Control B was a mixture of 1.3 µm particles (20%) and 8.0 µm particles (80%), and Control C was a 50:50 mixture (weight) of particles of the two sizes.

The reagent formulations were used to prepare the following elements having the reagents as capture probes for an assay:

| Variation | 1 | 2 | 3 | 4 | Corona Treatment? |
|---|---|---|---|---|---|
| 1 | Invention | Control A | Control B | Control C | No |
| 2 | Invention | Control A | Control B | Control C | Yes - 8 seconds |

The elements were prepared by heating a sheet of poly (ethylene terephthalate)/polyethylene laminate (SCOTCHPAK™ 241, 3M Co.) at a forming station (or mold) to form an array of depressed areas (hereinafter, "blisters") toward one side of the sheet, so that upon lamination to a cover sheet at a later time, the resulting pouch had narrow channels leading from the blisters to a main channel analogous to the devices described in U.S. Ser. No. 339,923 (filed Apr. 17, 1989 by Schnipelsky et al). Each blister was later filled with an appropriate reagent composition. A sheet was laminated to form a cover over the blisters and channel areas, and sealed to create a burst seal between each blister and the channel leading from it to the main channel. First, however, one section near the end of the main channel was treated with corona discharge from an Enercon DYNE-A-MITE™ corona discharge unit at 0.95 cm clearance to a TEFLON™ dielectric plate for 8 seconds. The reagent formulations described above (Invention & Controls A-C) were then immediately deposited in four spots on the treated surface to form an element, each spot having 0.9 to 1.1 µl of formulations noted above, in a row. The disposed formulations were dried for about 20 seconds in a stream of air at room temperature while heating the opposite side of the support with an iron at about 95° C. Another set of elements were similarly prepared but without the corona discharge treatment.

The blisters formed in the device were filled with the desired reagents. A first blister of each element was adapted to receive a specimen to be tested and to hold it during heating. A second blister was filled with a streptavidin-horseradish peroxidase conjugate composition as described above. A third blister contained a 1% sodium decylsulfate wash solution (in phosphate buffered saline solution containing 10 mmolar sodium phosphate, 150 mmolar sodium chloride and 1 mmolar ethylenediaminetetraacetic acid, pH 7.4), and a fourth blister contained the leuco dye composition described above. A last blister located at the end of the main channel was larger than the others and fitted with an absorbent to be a reservoir for waste fluids.

The cover sheet was then laminated and sealed in three steps. First the sandwich was pressed and sealed by heating at about 149° C. only around the blisters containing the 3 reagent solutions and around the waste blister. The formation of the sample-receiving PCR blister, including burst seals, and the channels was completed by heating the test pack between appropriately shaped heating jaws at about 163° C. The third step was the formation of perimeter seals around the test pack, and resealing all blister perimeter seals using a top plate temperature of 199° C. while the bottom plate remained at ambient temperature. The channels formed in the completed element were located so that passage of a roller across the portion of the element containing the blisters would sequentially burst the seals of the blisters and force the reagent from each blister into and along an exit channel to the main channel leading to the area containing the capture probes.

The completed integral test elements were used to evaluate the reagent formulations as follows:

A blister in the test device was filled with about 205–210 µl of a solution of a biotinylated oligonucleotide reagent used as a target nucleic acid which had a nucleotide sequence complementary to that of the oligonucleotide covalently bound to the polymer particles (that is, the nucleic acid reagent), and sealed. The sequence of that biotinylated target nucleic acid was as follows:

SEQ ID NO:5:

5'-X-AATCCTGGTT AGAATATAAA AGATAAT-3' wherein X is a single tetraethylene glycol linking group for attachment to biotin. The concentration of the target nucleic acid in the PCR reaction solution was believed to be 40 pmolar.

The blister containing this reagent was preheated to 95°–98° C. for 120 seconds and then rolled to break the seal and advance the solution to the area containing the nucleic acid reagent. The oligonucleotide reagent and capture reagent were hybridized in the detection blister during incubation at 42° C. for 5 minutes while the blister containing the conjugate of avidin-horseradish peroxidase was heated to 35° C. The seal of the conjugate blister was broken, and the solution directed to the detection area, where the avidin complexed with the available biotinylated reagent. The seal of the wash solution blister (preheated to 55° C. for 300 seconds) was broken and the wash solution directed to the detection area to clean out the main channel and to remove unbound conjugate from the detection area. The seal of the blister containing the dye-forming composition was then broken and the composition directed to the detection area. Incubation for 5 minutes proceeded to allow for dye formation before reading the color density scores.

The color density scores, provided in Table I below, were evaluated for two features: "quality of dye spot" and "color of dye spot".

The "quality of dye spot" was judged on a 1 to 5 score basis with each score having the following evaluation (with the lower scores being desired):

1 Good spot, no flaking or defects visually detected,

2 Pitting or very slight flaking (less than 25% of spot),

3 Slight flaking (about 25% of spot),

4 Significant flaking (25–75% of spot),

5 Spot completely flaked off.

The "color of dye spot" was evaluated by visual comparison of the wet dye density to a color chart, where 0 is no density and 10 is highest density. A high score is desirable here. The aggregate of the "quality" and "color" scores indicates whether the reagent formulation improved adhesion ("quality"), detracted from signal ("color") generated, or both.

TABLE I

| Variation | 1 (Invention) | 2 (Control A) | 3 (Control B) | 4 (Control C) |
|---|---|---|---|---|
| "Quality of Dye Spot" | | | | |
| 1 (dry) | 1.17 | 2.08 | 1.25 | 1.83 |
| 1 (wet) | 4.08 | 4.75 | 4.66 | 4.25 |
| 2 (dry) | 1.00 | 1.00 | 1.00 | 1.08 |
| 2 (wet) | 1.08 | 1.83 | 1.58 | 1.83 |

TABLE I-continued

| Variation | 1 (Invention) | 2 (Control A) | 3 (Control B) | 4 (Control C) |
|---|---|---|---|---|
| | "Color of Dye Spot" | | | |
| 1 | 6.0 (9 of 12 spots washed away) | 5.33 (9 of 12 spots washed away) | 6.0 (10 of 12 spots washed away | 6.80 (7 of 12 spots washed away |
| 2 | 7.42 | 6.67 | 6.92 | 7.75 |

The conclusions reached from the data presented in Table I include:

1) The elements having non-corona treated supports exhibited acceptable dye density (that is, sensitivity), but many reagents were washed away (that is, insufficient adhesion).
2) The reagent formulations containing larger particles generally were more opaque and provided lower spot quality and color.
3) The best "quality of dye spot" score was achieved with the small particle reagent formulation (both wet and dry).
4) The mixture of beads (two sizes) generally failed to provide the desired combination reagent adhesion and dye density.

EXAMPLE 4

Amplification and Detection of Nucleic Acid Using Leuco Dye Composition Containing Agarose This example demonstrates the practice of the preferred method of this invention using a leuco dye composition containing agarose.

A latex dispersion of poly[styrene-co-3-(p-vinylbenzylthio)propionic acid] (97.6:2.4 molar ratio) particles was prepared using the conventional technology described above, and the oligonucleotides described below were covalently attached to separate samples of the particles using the procedures described in U.S. Ser. No. 539,774 (filed Jun. 18, 1990 by Sutton et al). The oligonucleotides were linked to the particles through two tetraethylene glycol spacer units, a 3-amino-1,2-propanediol moiety and a thymine base according to the teaching of U.S. Pat. No. 4,962,029 (Levenson et al)

The oligonucleotides had the following sequences:
SEQ ID NO:6:
  5'-ATCCTGGGAT TAAATAAAAT AGTAAGAATG TATAGCCCTA C-X-3' and
SEQ ID NO:7:
  5'-CCTCAAACAG ACACCATGGT GCACCTGACT C-X-3'
wherein X is the linking group described above. The particulate reagents were prepared and formulated with the polymeric adhesive as described in Example 1, except that two sets of samples were prepared for each reagent so that the dry weight ratio of particulate reagent to adhesive was 4:0.1 in one set and 2:0.1 in the other set. The reagent having SEQ ID NO:6: was used to detect amplified target nucleic acid while the reagent having SEQ ID NO:7: was used as a Control reagent since the oligonucleotide is complementary to a sequence of β-globin DNA. Thus, the Control reagent was used as a "nonsense" reagent and when the assay was properly carried out, it provided no dye signal.

The reagents were used to prepare a series of analytical test elements containing the reagents as capture probes in assays for HUT/HIV-DNA. The elements were prepared to present a dilution series with respect to the amount of agarose contained in the dye-providing composition used in the elements.

The elements were prepared by heating a sheet of poly (ethylene terephthalate)/polyethylene laminate (SCOTCHPAK™ 241, 3M Co.) at a forming station (or mold) to form an array of depressed areas (hereinafter "blisters") toward one side of the sheet, and a larger blister near the end, and at the other side of the sheet, to which a main channel ultimately leads, a main channel from the first blister to the last, and tributary channels from each blister to the main channel so that upon lamination to a cover sheet at a later time, the resulting pouch had narrow channels leading from the blisters to a main channel analogous to the devices described in U.S. Ser. No. 339,923 (noted above). Each blister except the one at each end of the main channel was later filled with an appropriate reagent composition. A sheet was laminated to form a cover over the blisters and channel areas, and sealed to create a burst seal between each blister (except the last one) and the channel leading from it to the main channel. First, however, the cover sheet was treated with corona discharge using a conventional coating machine. The particulate reagent formulations described above (Invention & Control) were then immediately deposited in four spots on the treated surface to form an element, each spot having 0.9 to 1.1 µl of formulation noted above, in a row. The disposed formulations were dried for about 20 seconds in a stream of air at room temperature while heating the opposite side of the support with an iron at about 95° C.

The blisters formed in the device were filled with the desired reagents. A first blister of each element was adapted to receive a specimen to be tested and to hold it during heating. A second blister was filled with a sodium decyl sulfate (1%) wash solution (350 µl, in phosphate buffered saline solution containing 10 mmolar sodium phosphate, 150 mmolar sodium chloride and 1 mmolar ethylenediaminetetraacetic acid, pH 7.4). A third blister was filled with a streptavidin-horseradish peroxidase conjugate composition (235 µl) as described above, and a fourth blister contained the leuco dye composition (510 µl) described below.

A series of leuco dye compositions were prepared, containing from 0 to 5% agarose:

The leuco dye dispersion described above for Example 3 (24.75 ml) was mixed with the amounts of dimedone solution and agarose as noted in the following table:

| Leuco Dye Dispersion | 0.25 molar Dimedone | Agarose (g, %) |
|---|---|---|
| 24.75 ml | 0.25 ml | 1.25, 5 |
| 24.75 ml | 0.25 ml | 1.00, 4 |
| 24.75 ml | 0.25 ml | 0.75, 3 |
| 24.75 ml | 0.25 ml | 0.50, 2 |
| 24.75 ml | 0.25 ml | 0.38, 1.5 |
| 24.75 ml | 0.25 ml | 0.25, 1 |
| 24.75 ml | 0.25 ml | 0.125, 0.5 |
| 24.75 ml | 0.25 ml | 0.06, 0.25 |
| 24.75 ml | 0.25 ml | 0, 0 |

The last blister of the elements, at the end of the main channel, was larger than the others and fitted with an absorbent material conventional to the art to be a reservoir for waste fluids.

The cover sheet was then laminated and sealed in three steps. First, the sandwich of layers was pressed and sealed by heating at about 149° C. only around the blisters containing the 3 reagent solutions and around the waste blister. The formation of the sample-receiving PCR blister, including burst seals, and the channels was completed by heating the resulting element between appropriately shaped heating jaws at about 163° C. The third step was the formation of perimeter seals around the test pack, and resealing all blister perimeter seals using a top plate temperature of 199° C. while the bottom plate remained at ambient temperature. The channels formed in the completed element were located so that passage of a roller across the portion of the element containing the blisters would sequentially burst the seals of the blisters and force the reagent from each blister into and along an exit channel to the main channel leading to the area containing the capture probes. Note that the finished element is inverted so that the cover sheet containing the capture probe deposits is the bottom of the finished element with the probe deposits properly aligned in the main channel to form a detection area.

The completed integral test elements were used to evaluate the reagent formulations as follows:

A blister in each element was filled (190–210 μl) with a PCR reagent mix prepared as follows: A target HUT/HIV-I DNA nucleic acid present at about 12,500 copies/250 μl was formulated with tris(hydroxymethyl)aminomethane buffer (10 mmolar, pH 8), potassium chloride (50 mmolar), magnesium chloride (10 mmolar), gelatin (0.1 mg/ml), each of the primers identified below (SEQ ID NO:8 and SEQ ID NO:9, 1 pmolar of each), DATP, dCTP, dGTP and dTTP (1.5 mmolar of each), human placental DNA (2.5 μg) and DNA polymerase from Thermus aquaticus (40 units/250 μl, 7.1 nmolar).

SEQ ID NO:8:

5'-X-TTTGGTCCTT GTCTTATGTC CAGAATGC-3'SEQ ID NO:9:

5'-ATAATCCACC TATCCCAGTA GGAGAAAT-3' wherein X represents biotin and two tetraethylene glycol spacer units attached to the oligonucleotide according to the teaching of U.S. Pat. No. 4,914,210.

The following PCR protocol was carried out in a 0.5 ml microcentrifuge tube using a commercially available Perkin Elmer THERMAL CYCLER™:

The target nucleic acid was denatured by heating it to 90° C. for about 15 seconds. After cooling to 55° C. for 30 seconds to anneal the primers to the target nucleic acid, primer extension products were then formed at 70° C. for about 30 seconds, followed by denaturation again at 95° C. The cycle of annealing, primer extension and denaturation was carried out 35 times.

The blister containing the amplified target nucleic acid in each element was preheated to about 97° C. and then the blister was pressed to break the seal and advance the solution to the detection area containing the four immobilized capture probes. The amplified target nucleic acid was then hybridized to the probe reagents at 42° C. for five minutes while the blister containing the wash solution was preheated to 55° C. Then the wash solution blister was burst and the wash solution was forced into the detection area to remove unbound target nucleic acid. Without preheating, the seal of the blister containing the enzyme-labeled conjugate was broken, forcing the conjugate into the detection area to react with immobilized amplified target nucleic acid over a five minute period. During this time, the leuco dye composition was preheated to 55° C., and the seal of the blister was then broken and the composition was forced to the detection station where it displaced the unbound conjugate. Dye formation was allowed to proceed for five minutes before the dye signals were read. A second reading was made after an additional five minutes. The color of each probe region was evaluated by comparing the wet dye density with a color chart where 0 represented no density and 10 represented the highest density. A high dye density for the target nucleic acid and a low score for the Control probes was desired. Two tests were carried out simultaneously for each experiment. The resulting dye signals are shown in the following table.

| | | Dye Signal**** | | | | |
|---|---|---|---|---|---|---|
| | | Controls** Particles/Adhesive | | Invention** Particles/Adhesive | | |
| Sample | Agarose (%)* | 4/0.1 (5/10 min.) | 2/0.1 (5/10 min.) | 4/0.1 (5/10 min.) | 2/0.1 (5/10 min.) | Channel Signal*** |
| 1 | 5 | 0/0 | 0/0 | 0/0 | 0/0 | NO |
| 1 | 5 | 0-F/0 | 1/1 | 5/6 | 6/6 | NO |
| 2 | 4 | 1-F/2 | 1/2 | 6/7 | 6/7 | YES |
| 2 | 4 | 1-F/2 | 1/2 | 6/7 | 5/7 | NO |
| 3 | 3 | 0/0 | 0/0 | 6/6 | 5/7 | NO |
| 3 | 3 | 0.5/1 | 0/1 | 5.5/5 | 5.5/5 | NO |
| 4 | 2 | 0-G/0 | 0/0 | 4/6 | 5/7 | NO |
| 4 | 2 | 0-G/0 | 0/0 | 6/7 | 6/7 | NO |
| 5 | 1.5 | 0-F/0 | 0/0 | 5/7 | 5/7 | NO |
| 5 | 1.5 | G | 1/0 | 5/7 | 5/7 | NO |
| 6 | 1 | 0-F/0 | 0-F/0 | 5/7 | 5/7 | NO |
| 6 | 1 | G | 1/1 | G | 7/8 | NO |
| 7 | 0.5 | 0-F-G/0-F | 0/0 | 2/2 | 6/7 | YES |
| 7 | 0.5 | 0-F/0 | 1-F/0 | G | 6/7 | NO |
| 8 | 0.25 | 0-F-G/0-F | 0/1 | 4-F/5 | 5/7 | NO |
| 8 | 0.25 | G | 1/2 | 4-F/5 | 5/7 | YES |

| | | Dye Signal**** | | | | |
|---|---|---|---|---|---|---|
| | | Controls** Particles/Adhesive | | Invention** Particles/Adhesive | | |
| Sample | Agarose (%)* | 4/0.1 (5/10 min.) | 2/0.1 (5/10 min.) | 4/0.1 (5/10 min.) | 2/0.1 (5/10 min.) | Channel Signal*** |
| 9 | 0 | 1-F/2 | 2/3 | 5/7 | 5/7 | YES |
| 9 | 0 | G | 1/2 | 5/6 | 5/6 | YES |

\* The agarose concentration was from 0 to 5%.
\*\*"F" means the particulate reagent was partially removed from the substrate.
"G" means that the reagent was completely removed.
"F-G" means that the reagent was mostly removed.
\*\*\*This column indicates whether the color signal was at the probe area only, or if it was also spread out downstream from that area. The presence of color signal downstream is believed to be due to the lack of a wash after reaction of the labeled avidin conjugate.
\*\*\*\*The dye signal was evaluated after 5 and 10 minutes ("5/10 min") after the beginning of dye development.

The results obtained in this example show the "controls" exhibited very low color signals for all levels of agarose. Also, there was good color signals for the target nucleic acid at all levels of agarose. The dye-providing compositions having agarose levels above 2% were difficult to dispense. Below the agarose concentration of about 0.5%, there was a tendency of the color signal to spread downstream into the channel, so the amount preferably is not below about 0.25%.

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A method for the detection of a target nucleic acid comprising:

A. contacting a specimen suspected of containing a target nucleic acid with a nucleic acid test element comprising a sealable support having disposed thereon a nucleic acid reagent composition comprising a mixture of:
  a. a nucleic acid reagent comprising: particles composed of a first polymer having a glass transition temperature of at least about 70° C., said particles having an average diameter of from about 0.1 to about 3 micrometers, and
    an oligonucleotide covalently attached to said particles which is complementary to said target nucleic acid, and
  b. a water insoluble adhesive comprising a second polymer which has a glass transition temperature which is at least about 30° C. less than the glass transition temperature of said first polymer,
    said polymeric adhesive being present in said composition at from about 1 to about 20 weight percent,
    wherein said sealable support has hydrophilic surface groups provided by a treatment selected from the group consisting of corona discharge treatment, chromic acid treatment, and treatment with a radio frequency electromagnetic field in the presence of a reactive gas, or said hydrophilic surface groups are provided by a hydrophilic subbing layer on which said composition is disposed,
    so as to form a water insoluble hybridized product of said target nucleic acid and said oligonucleotide, and B. detecting said hybridized product as an indication of the presence of said target nucleic acid in said specimen.

2. The method of claim 1 for the detection of a viral or bacterial nucleic acid.

3. The method of claim 2 for the detection of HIV-I DNA.

4. The method of claim 1 for the detection of a bacterial or genomic nucleic acid.

5. The method of claim 1 wherein said detection is accomplished using a water soluble, detection oligonucleotide which can be directly or indirectly hybridized with said target nucleic acid.

6. The method of claim 5 wherein said water soluble detection oligonucleotide is labeled with a specific binding material, and detection is accomplished from reaction of said specific binding material with a detectable receptor therefor.

7. The method of claim 1 carried out in a self-contained test device.

8. The method of claim 1 wherein said target nucleic acid is amplified prior to step A.

9. The method of claim 8 wherein amplification is carried out using a polymerase chain reaction with two primers complementary to the complementary strands of said target nucleic acid.

10. The method of claim 9 wherein at least one of said primers is biotinylated.

11. The method of claim 10 wherein said amplified target nucleic acid is detected by reacting said amplified target nucleic acid with at avidin which is labeled with an enzyme, and contacting said reaction product with a dye-providing composition which provides a calorimetric or chemiluminescent signal in response to said enzyme.

12. The method of claim 11 wherein said dye-providing composition further comprises from about 0.1 to about 3 weight % of a water insoluble macromolecular weight material which exhibits shear thinning to a viscosity of less than about 1 poise but with very little shear force or agitation.

13. The method of claim 12 wherein said water insoluble macromolecular weight material is agarose.

14. The method of claim 11 wherein said enzyme label is peroxidase.

15. The method of claim 1 wherein said polymeric particles have an average diameter of from about 0.5 to about 2 micrometers.

16. The method of claim 1 wherein said first polymer glass transition temperature is from about 70° to about 175° C., and said second polymer glass transition is from about 30 to about 120° C. less than said first polymer glass transition temperature.

17. The method of claim 1 wherein said adhesive is present in said composition at from about 2 to about 10 weight precent.

18. The method of claim 1 wherein said first polymer comprises:
   a. from about 0.1 to 60 weight percent of recurring units derived from one or more ethylenically unsaturated polymerizable monomers having a reactive group selected from the group consisting of an active halogen, carboxy, amidine, activated 2-substituted ethylsulfonyl, activated 2-substituted ethylcarbonyl, an active ester, vinylsulfonyl, vinylcarbonyl, aldehyde, hydrazine, epoxy, amino and sulfhydryl,
   b. from about 60 to about 99.9 weight percent of recurring units derived from one or more ethylenically unsaturated polymerizable monomers which provide hydrophobicity, and
   c. from 0 to about 15 weight percent of recurring units derived from one or more ethylenically unsaturated polymerizable monomers other than those defined in (a) and (b), and said second polymer comprises:
   d. from about 55 to 100 weight percent of recurring units derived from one or more ethylenically unsaturated polymerizable monomers which provide hydrophobicity,
   e. from 0 to about 45 weight percent of recurring units derived from one or more ethylenically unsaturated polymerizable monomers which form a water soluble homopolymer or which provide hydrophilicity, and
   f. from 0 to about 15 weight percent of recurring units derived from one or more ethylenically unsaturated polymerizable monomers which provide crosslinking in said second polymer.

19. The method of claim 18 wherein said polymeric particles comprise from about 2 to about 15 weight percent of component (a), from about 85 to about 98 weight percent of component (b), and from 0 to about 10 weight percent of component (c).

20. The method of claim 18 wherein the monomers of component (a) have reactive groups selected from the group consisting of an active halogen, carboxy, activated 2-substituted ethylsulfonyl and vinylsulfonyl.

21. The method of claim 1 wherein said composition is disposed in a defined region of said support.

22. A method for the amplification and detection of a target nucleic acid comprising:

A. amplifying a target nucleic acid using at least one biotinylated primer to form at least one amplified biotinylated target nucleic acid,
B. contacting said amplified biotinylated target nucleic acid with a nucleic acid test element comprising a sealable support having disposed thereon a nucleic acid reagent composition comprising a mixture of:
   a. a nucleic acid reagent comprising: particles composed of a first polymer having a glass transition temperature of at least about 70° C., said particles having an average diameter of from about 0.1 to about 3 micrometers, and
      an oligonucleotide covalently attached to said particles which is complementary to said target nucleic acid, and
   b. a water insoluble adhesive comprising a second polymer which has a glass transition temperature which is at least about 30° C. less than the glass transition temperature of said first polymer,
      said polymeric adhesive being present in said composition at from about 1 to about 20 weight percent,
      wherein said sealable support has hydrophilic surface groups provided by a treatment selected from the group consisting of corona discharge treatment, chromic acid treatment and treatment with a radio frequency electromagnetic field in the presence of a reactive gas, and or said hydrophilic surface groups are provided by a hydrophilic subbing layer on which said composition is disposed,
      to form a water insoluble immobilized hybridized product of said amplified biotinylated target nucleic acid and said nucleic acid reagent on said element, and
C. detecting the presence of said immobilized hybridized product by complexation of said amplified biotinylated target nucleic acid with a labeled conjugate of avidin as an indication of the presence of said target nucleic acid.

23. The method of claim 22 wherein said labeled conjugate of avidin comprises an enzyme, and detection of the hybridized product is accomplished by contacting it with a composition which provides a colorimetric or chemiluminescent signal in the presence of said enzyme.

24. The method of claim 23 wherein said signal providing composition comprises: a leuco dye which provides a dye in the presence of hydrogen peroxide and peroxidase, and from about 0.1 to about 3 weight % of agarose.

* * * * *